United States Patent
Ruchala et al.

(10) Patent No.: US 8,406,844 B2
(45) Date of Patent: Mar. 26, 2013

(54) METHOD FOR MODIFICATION OF RADIOTHERAPY TREATMENT DELIVERY

(75) Inventors: Kenneth J. Ruchala, Madison, WI (US); Gustavo H. Olivera, Madison, WI (US); Jeffrey M. Kapatoes, Madison, WI (US); Paul J. Reckwerdt, Madison, WI (US); Weiguo Lu, Madison, WI (US); John H. Hughes, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 1765 days.

(21) Appl. No.: 10/506,866

(22) PCT Filed: Mar. 6, 2003

(86) PCT No.: PCT/US03/07014
§ 371 (c)(1), (2), (4) Date: May 16, 2005

(87) PCT Pub. No.: WO03/076003
PCT Pub. Date: Sep. 18, 2003

(65) Prior Publication Data
US 2005/0201516 A1      Sep. 15, 2005

Related U.S. Application Data

(60) Provisional application No. 60/362,112, filed on Mar. 6, 2002.

(51) Int. Cl.
   *A61B 5/05* (2006.01)
(52) U.S. Cl. ........ 600/407; 600/408; 600/411; 600/415; 600/427; 378/65
(58) Field of Classification Search .......... 600/407–408, 600/411, 415, 427; 378/65
See application file for complete search history.

(56) References Cited

U.S. PATENT DOCUMENTS

| | | | |
|---|---|---|---|
| 4,998,268 | A | 3/1991 | Winter |
| 5,008,907 | A | 4/1991 | Norman et al. |
| 5,027,818 | A | 7/1991 | Bova et al. |
| 5,044,354 | A | 9/1991 | Goldhorn et al. |

(Continued)

FOREIGN PATENT DOCUMENTS

| | | |
|---|---|---|
| CA | 2091275 | 9/1993 |
| JP | 63209667 | 8/1988 |

(Continued)

OTHER PUBLICATIONS

K.J. Ruchala, G.H. Olivera, J.M. Kapatoes, R. Jeraj, P.J. Reckwerdt and W. Lu; Multi-Margin Optimization with Daily Selection (mmods) for Image-Guided Radiotherapy; International Journal of Radiation Oncology Biology Physics, Oct. 1, 2002, p. 318, vol. 54, Issue 2, Supplement 1, Elsevier Science Inc., United States. Also available online Sep. 20, 2002.

(Continued)

*Primary Examiner* — James Kish
(74) *Attorney, Agent, or Firm* — Michael Best & Friedrich LLP

(57) ABSTRACT

A method of contoured-anatomy dose repositioning (CADR) as a means to automatically reposition a patient to better recover the planned dose distribution without reoptimizing the treatment plan. CADR utilizes planning CT images, the planned dose distribution, and on-line images for repositioning dose distribution on a given day. Contours are also placed upon the images using manual, automatic, template-based, or other techniques. CADR then optimizes the rigid-body repositioning of the patient so that the daily dose distribution closely matches the planned dose distribution.

30 Claims, 6 Drawing Sheets

U.S. PATENT DOCUMENTS

| | | |
|---|---|---|
| 5,117,829 A | 6/1992 | Miller et al. |
| 5,138,647 A | 8/1992 | Nguyen et al. |
| 5,317,616 A | 5/1994 | Swerdloff et al. |
| 5,332,908 A | 7/1994 | Weidlich |
| 5,335,255 A | 8/1994 | Seppi et al. |
| 5,351,280 A | 9/1994 | Swerdloff et al. |
| 5,391,139 A | 2/1995 | Edmundson |
| 5,394,452 A | 2/1995 | Swerdloff et al. |
| 5,442,675 A | 8/1995 | Swerdloff et al. |
| 5,446,548 A | 8/1995 | Gerig et al. |
| 5,471,516 A | 11/1995 | Nunan |
| 5,511,549 A | 4/1996 | Legg et al. |
| 5,528,650 A | 6/1996 | Swerdloff et al. |
| 5,548,627 A | 8/1996 | Swerdloff et al. |
| 5,552,605 A | 9/1996 | Arata |
| 5,579,358 A | 11/1996 | Lin |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,712,482 A | 1/1998 | Gaiser et al. |
| 5,724,400 A | 3/1998 | Swerdloff et al. |
| 5,751,781 A | 5/1998 | Brown et al. |
| 5,754,622 A | 5/1998 | Hughes |
| 5,754,623 A | 5/1998 | Seki |
| 5,760,395 A | 6/1998 | Johnstone |
| 5,815,547 A | 9/1998 | Shepherd et al. |
| 5,818,902 A | 10/1998 | Yu |
| 5,823,192 A | 10/1998 | Kalend et al. |
| 5,835,562 A | 11/1998 | Ramsdell et al. |
| 5,949,080 A | 9/1999 | Ueda et al. |
| 5,983,424 A | 11/1999 | Naslund |
| 6,038,283 A | 3/2000 | Carol et al. |
| 6,049,587 A | 4/2000 | Leksell et al. |
| 6,144,875 A | 11/2000 | Schweikard et al. |
| 6,198,957 B1 | 3/2001 | Green |
| 6,241,670 B1 | 6/2001 | Nambu |
| 6,260,005 B1 | 7/2001 | Yang et al. |
| 6,279,579 B1 | 8/2001 | Riaziat et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,422,748 B1 | 7/2002 | Shepherd et al. |
| 6,424,856 B1 | 7/2002 | Vilsmeier et al. |
| 6,438,202 B1 | 8/2002 | Olivera et al. |
| 6,477,229 B1 | 11/2002 | Grosser |
| 6,504,899 B2 | 1/2003 | Pugachev et al. |
| 6,510,199 B1 | 1/2003 | Hughes et al. |
| 6,516,046 B1 | 2/2003 | Frohlich et al. |
| 6,527,443 B1 | 3/2003 | Vilsmeier et al. |
| 6,539,247 B2 | 3/2003 | Spetz |
| 6,560,311 B1 | 5/2003 | Shepard et al. |
| 6,618,467 B1 | 9/2003 | Ruchala et al. |
| 6,636,622 B2 | 10/2003 | Mackie et al. |
| 6,661,870 B2 | 12/2003 | Kapatoes et al. |
| 6,690,965 B1 | 2/2004 | Riaziat et al. |
| 6,714,629 B2 | 3/2004 | Vilsmeier |
| 6,731,970 B2 | 5/2004 | Schlossbauer et al. |
| 6,735,277 B2 | 5/2004 | McNutt et al. |
| 6,741,674 B2 | 5/2004 | Lee |
| 6,757,355 B1 | 6/2004 | Siochi |
| 6,774,383 B2 | 8/2004 | Norimine et al. |
| 6,792,073 B2 | 9/2004 | Deasy et al. |
| 6,792,074 B2 | 9/2004 | Erbel et al. |
| 6,804,548 B2 | 10/2004 | Takahashi et al. |
| 6,842,502 B2 | 1/2005 | Jaffray et al. |
| 6,865,253 B2 | 3/2005 | Blumhofer et al. |
| 6,865,254 B2 | 3/2005 | Nafstadius |
| 6,865,411 B2 | 3/2005 | Erbel et al. |
| 6,871,171 B1 | 3/2005 | Agur et al. |
| 6,882,702 B2 | 4/2005 | Luo |
| 6,888,919 B2 | 5/2005 | Graf |
| 6,904,125 B2 | 6/2005 | Van Dyk et al. |
| 6,914,959 B2 | 7/2005 | Bailey et al. |
| 6,961,405 B2 | 11/2005 | Scherch |
| 7,015,490 B2 | 3/2006 | Wang et al. |
| 7,046,762 B2 | 5/2006 | Lee |
| 7,221,733 B1 | 5/2007 | Takai et al. |
| 7,265,356 B2 | 9/2007 | Pelizzari et al. |
| 7,289,599 B2 | 10/2007 | Seppi et al. |
| 7,362,848 B2 | 4/2008 | Saracen et al. |
| 7,391,026 B2 | 6/2008 | Trinkaus et al. |
| 7,412,029 B2 | 8/2008 | Myles |
| 7,438,685 B2 | 10/2008 | Burdette et al. |
| 7,450,687 B2 | 11/2008 | Yeo et al. |
| 7,492,858 B2 | 2/2009 | Partain et al. |
| 7,496,173 B2 | 2/2009 | Goldman et al. |
| 7,505,559 B2 | 3/2009 | Kuduvalli |
| 7,513,861 B2 | 4/2009 | Klein et al. |
| 7,519,150 B2 | 4/2009 | Romesberg et al. |
| 7,551,717 B2 | 6/2009 | Tome et al. |
| 7,590,440 B2 | 9/2009 | Lu et al. |
| 7,620,144 B2 | 11/2009 | Bodduluri |
| 7,639,854 B2 | 12/2009 | Schnarr et al. |
| 7,693,257 B2 | 4/2010 | Allison |
| 7,708,682 B2 | 5/2010 | Pekar et al. |
| 7,831,289 B2 | 11/2010 | Riker et al. |
| 7,853,308 B2 | 12/2010 | Sauer et al. |
| 7,907,987 B2 | 3/2011 | Dempsey |
| 7,945,022 B2 | 5/2011 | Nelms et al. |
| 8,073,104 B2 | 12/2011 | Yan et al. |
| 8,085,899 B2 | 12/2011 | Nord et al. |
| 8,125,813 B2 | 2/2012 | Nizin et al. |
| 8,175,350 B2 | 5/2012 | Suri et al. |
| 2001/0033682 A1* | 10/2001 | Robar et al. .................. 382/132 |
| 2002/0080915 A1* | 6/2002 | Frohlich ........................ 378/65 |
| 2002/0193685 A1 | 12/2002 | Mate et al. |
| 2003/0083562 A1 | 5/2003 | Bani-hashemi et al. |
| 2003/0212325 A1 | 11/2003 | Cotrutz et al. |
| 2004/0068182 A1 | 4/2004 | Misra |
| 2004/0254448 A1 | 12/2004 | Amies et al. |
| 2005/0096515 A1 | 5/2005 | Geng |
| 2005/0143965 A1 | 6/2005 | Failla et al. |
| 2005/0251029 A1 | 11/2005 | Khamene et al. |
| 2006/0133568 A1 | 6/2006 | Moore |
| 2007/0041496 A1 | 2/2007 | Olivera et al. |
| 2007/0041500 A1 | 2/2007 | Olivera et al. |
| 2007/0156453 A1 | 7/2007 | Frielinghaus et al. |
| 2008/0008291 A1 | 1/2008 | Alakuijala et al. |
| 2008/0031406 A1 | 2/2008 | Yan et al. |
| 2008/0064953 A1 | 3/2008 | Falco |
| 2008/0279328 A1 | 11/2008 | Zeitler et al. |
| 2009/0041200 A1 | 2/2009 | Lu et al. |

FOREIGN PATENT DOCUMENTS

| | | |
|---|---|---|
| JP | 01-209077 | 8/1989 |
| JP | 6007464 | 1/1994 |
| JP | 10052421 | 2/1998 |
| JP | 10501151 | 2/1998 |
| JP | 10146395 | 6/1998 |
| JP | 11244401 | 9/1999 |
| JP | 2001-161839 | 6/2001 |
| JP | 2001-259060 | 9/2001 |
| JP | 2001340474 | 12/2001 |
| JP | 2002210029 | 7/2002 |
| JP | 2002522128 | 7/2002 |
| JP | 2002522129 | 7/2002 |
| JP | 2002355321 | 12/2002 |
| JP | 2003523220 | 8/2003 |
| JP | 2004166975 | 6/2004 |
| JP | 2004321502 | 11/2004 |
| JP | 2005160804 | 6/2005 |
| JP | 2007509644 | 4/2007 |
| JP | 2007516743 | 6/2007 |
| TW | 300853 | 3/1997 |
| WO | 9014129 | 11/1990 |
| WO | 9202277 | 2/1992 |

| WO | WO 98/02091 | 1/1998 |
| WO | 0007669 | 2/2000 |
| WO | WO 00/07669 | 2/2000 |
| WO | 0054689 | 9/2000 |
| WO | 03032838 | 4/2003 |
| WO | 03092789 | 11/2003 |
| WO | 03099380 | 12/2003 |
| WO | 2004080522 | 9/2004 |
| WO | 2004105574 | 12/2004 |
| WO | 2005031629 | 4/2005 |
| WO | 2005035061 | 4/2005 |
| WO | 2005057463 | 6/2005 |
| WO | 2005062790 | 7/2005 |
| WO | 2007133932 | 11/2007 |

OTHER PUBLICATIONS

Di Yan, Frank Vicini, John Wong and Alvaro Martinez, Adaptive Radiation Therapy, Phys. Med. Biol. 42, 1997, pp. 123-132, IOP Publishing Ltd., United Kingdom.

Di Yan and David Lockman, Organ/Patient Geometric Variation in External Beam Radiotherapy and Its Effects, Med. Phys. 28, Apr. 2001, Am. Assoc. Phys. Med.

Di Yan, D.Sc., D.A. Jaffray, Ph.D., and J.W. Wong, Ph.D., A Model to Accumulate Fractionated Dose in a Deforming Organ, Int. J. Radiation Oncology Biol. Phys., 1999, pp. 665-675, vol. 44, No. 3, Elsevier Science Inc., United States.

Lof, J., et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.

Office Action from Canadian Patent Office for Application No. 2478296 dated Jul. 2, 2009 (4 pages).

Office Action from European Patent Office for Application No. 03711462.6 dated Aug. 4, 2009 (4 pages).

Office Action from Japanese Patent Office for Application 2003-574268 dated Apr. 7, 2009 (english translation, 2 pages).

Purdy, James, "3D Treatment Planning and Intensity-Modulated Radiation Therapy," Oncology, vol. 13, No. 10, suppl. 5 (Oct. 1999).

Bert, Christoph, et al., "4D Treatment Planning for Scanned Ion Beams", BioMed Central, Radiation Oncology, 2:24, available online at: <http://www.ro-journal.com/content/2/1/24>, Jul. 3, 2007.

Birkner, M. et al., "Image guided adaptive IMRT of the prostate based on a probabilistic patient geometry," Radiotherapy and Oncology, vol. 64, Supplement 1, 21st Annual ESTRO Meeting, Sep. 21, 2002, p. S282, ISSN 0167-8140.

Yu, Cedric X., et al., "A Method for Implementing Dynamic Photon Beam Intensity Modulation using Independent Jaws and a Multileaf Collimator," Phys. Med. Biol. 40. 1995: 769-787.

Yan, Di, "On-line Strategy of Daily Dose Prescription in Adaptive Radiotherapy," Proceedings of the 22nd Annual EMBS International Conference, Jul. 23-28, 2000, Chicago, IL, pp. 2145-2148.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Mackie, T. Rockwell et al., "Tomotherapy" Seminars in Radiation Oncology, vol. 9, No. 1, Jan. 1, 1999, pp. 108-117, XP002603992.

Fitchard, E.E., et al., "Registration of Tomotherapy Patients Using CT Projection Files," www.madrad.radiology.wisc.edu/tomo/registration/reg_iccr2/reg_iccr2.html.

Ruchala, Kenneth, et al., "Adaptive IMRT with Tomotherapy", RT Image, vol. 14, No. 25, pp. 14-18, Jun. 18, 2001.

Rueckert, D.et al., "Nonrigid Registration Using Free-Form Deformations: Application to Breast MR Images", IEEE Transactions on Medical Imaging, vol. 18, No. 8, pp. 712-721, Aug. 1999.

Michalski, Jeff M. et al., Three-Dimensional Conformal Radiation Therapy (3DCRT) for Prostate Cancer,: The Prostate Cancer InfoLink, Jul. 6, 1996.

Mackie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," Xiith ICCR, May 27-30, 1997.

Office Action from Canadian Patent Office for Application No. 2478296 dated Nov. 26, 2007 (2 pages).

Office Action from European Patent Office for Application No. 03711462.6 dated Apr. 28, 2010 (4 pages).

Office Action from European Patent Office for Application No. 03711462.6 dated Dec. 14, 2007 (4 pages).

Office Action from European Patent Office for Application No. 03711462.6 dated Jun. 12, 2008 (5 pages).

Office Action from Japanese Patent Office for Application 2003-574268 dated Feb. 9, 2010 (with English translation, 4 pages).

PCT/US2003/07014, International Preliminary Examination Report, dated Jan. 14, 2004 (4 pages).

Supplementary Partial European Search Report from European Patent Office for Application No. 03711462.6 dated Dec. 15, 2005 (4 pages).

Decision to Refuse a European Patent Application from the European Patent Office for Application No. 03711462.6 dated May 24, 2011 (15 pages).

* cited by examiner

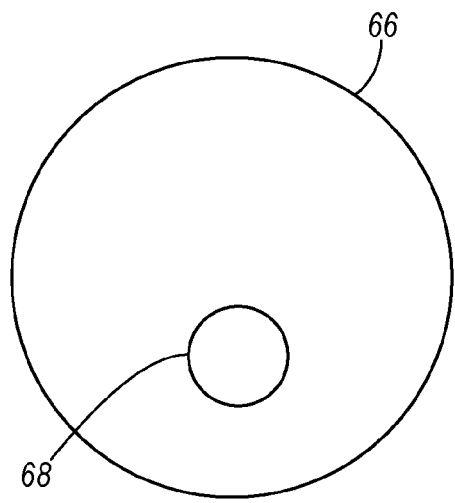
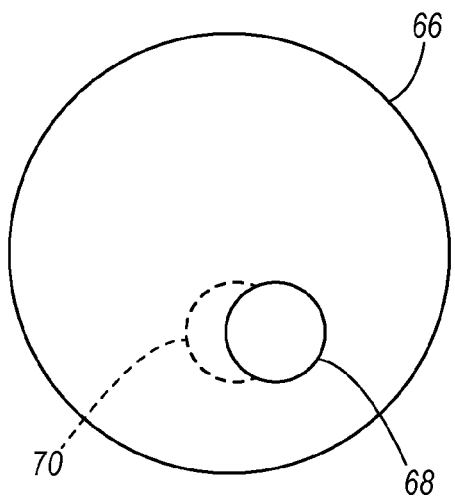
FIG. 3  FIG. 4
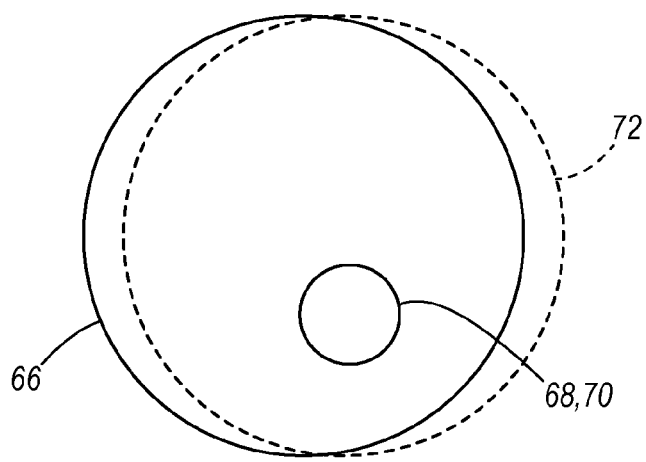
FIG. 5

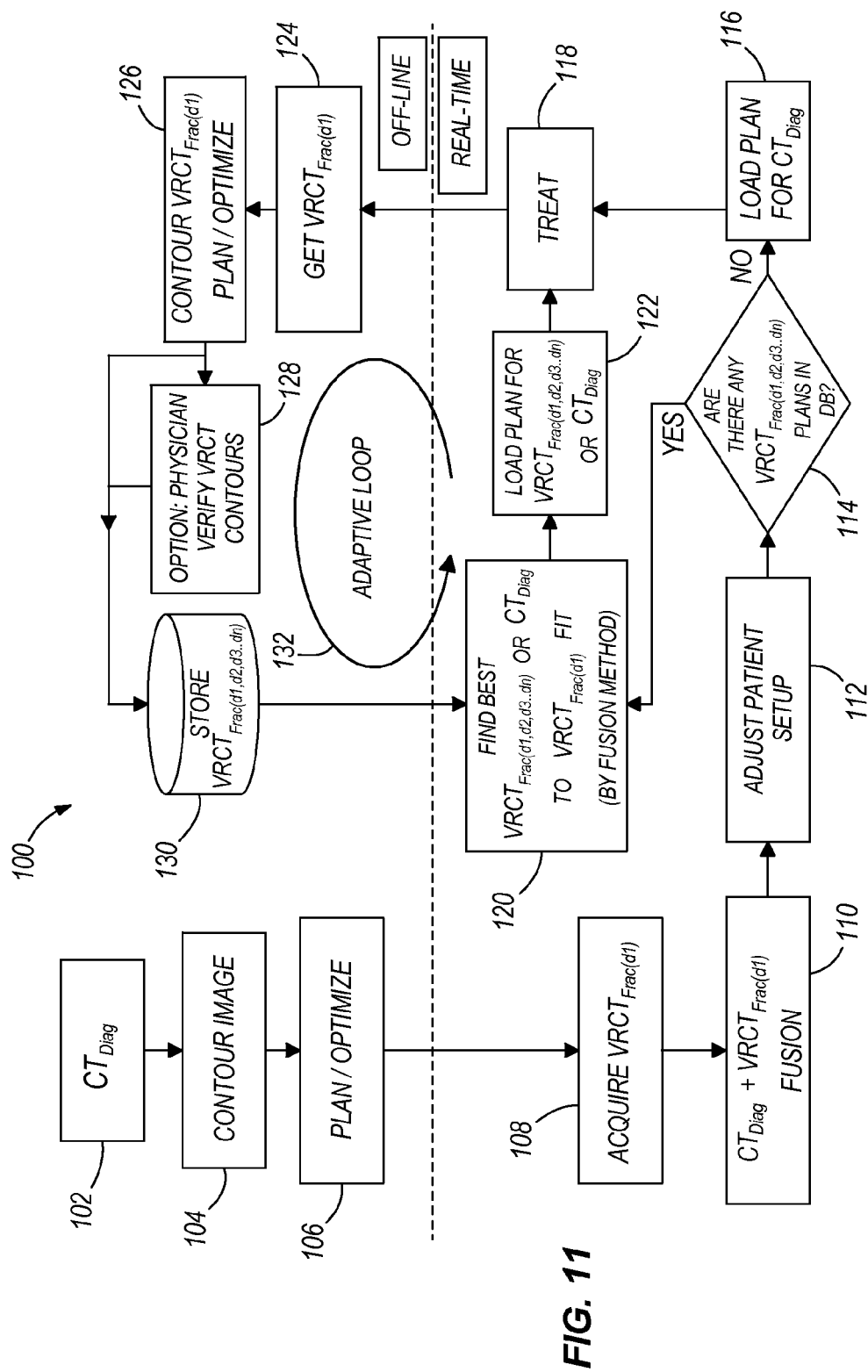

METHOD FOR MODIFICATION OF RADIOTHERAPY TREATMENT DELIVERY

CROSS-REFERENCE TO RELATED APPLICATIONS

This application is a 35 U.S.C. §371 application of PCT/US03/07014 filed on Mar. 6, 2003, which claims the benefit of U.S. Provisional Application No. 60/362,112, filed Mar. 6, 2002, the disclosure of which is incorporated herein by reference.

BACKGROUND OF THE INVENTION

This invention relates generally to intensity modulated radiation therapy for the treatment of cancer or the like, and specifically to a method for precisely delivering the dose of radiation to a displaced target.

Medical equipment for radiotherapy treats tumorous tissue with high energy radiation. The amount of radiation and its placement must be accurately controlled to ensure that the tumorous tissue receives sufficient radiation to be destroyed, and that the damage to the surrounding and adjacent non-tumorous tissue is minimized.

The radiotherapy process typically involves treatment planning and treatment delivery. The radiotherapy process commonly begins with the acquisition of three-dimensional patient images, such as a computed tomography (CT) image or a magnetic resonance image (MRI). Next, relevant anatomical structures are delineated or contoured. These structures can be classified as either target volumes to be irradiated, or sensitive structures to which radiation should be minimized. A treatment plan is then prepared that is optimized to maximize treatment to the target volumes while minimizing radiation to the sensitive structures.

Typically the tumor or target volume will be treated from several different angles with the intensity and shape of the radiation beam adjusted appropriately. The purpose of using multiple beams, which converge on the site of the tumor, is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form the treatment plan for the tumor.

Due to anatomical changes caused by tumor growth, breathing, organ movement or the like, the intended structures may not receive the planned dose, even if the radiation therapy machine operates perfectly. For example, the motion of target structures relative to sensitive structures could cause underdosing or overdosing of those structures, respectively. A "correct" patient set-up does not always result in the planned dose hitting the target. It would be beneficial to collect reliable patient images, or fraction images, immediately prior to treatment. Specifically, one could contour those images, and then optimize a new plan to treat the patient based on the current anatomical locations. However, this process is not generally fast enough to be performed on-line while the patient is on the treatment couch waiting to be treated. In principle, if reliable patient images or fraction images could be collected immediately prior to treatment, those images could be contoured, and then used to re-optimize a new plan to treat the patient based on current anatomical locations at the time of treatment. However, because the patient cannot remain motionless on the treatment couch for too long, this process is typically not fast enough, as any movement ultimately compromises newly acquired anatomical information.

One of the major efforts in radiotherapy has been in reducing the effect of treatment variations, such as beam placement errors and geometric variation of treatment targets and critical normal organs. To compensate for these variations, a pre-defined margin around the target volume is utilized. This is often referred to as the clinical target volume (CTV). Theoretically, the use of a margin will ensure that the target volume receives the intended dose, even if the target is somewhat displaced. Uncertainties in the treatment process often require the delineated tumor volume be enlarged by a margin to a planning target volume (PTV). This margin ensures that the tumor receives the intended target dose. Thus, through the long fractionated treatment, the tumor should always be contained within the PTV. However, too large a margin results in delivering unnecessary dose to healthy tissues, yet too small a margin could preclude the target from receiving the desired dose.

Over the course of radiotherapy treatment, the radiation is delivered in doses. A single dosage day is considered a dosage "fraction." From day to day, or even more frequently, internal organ motion can cause the target volume to move. Such movement presents a very significant source of imprecision. The problem is exacerbated as increasingly conformal treatments are attempted, such as through the use of intensity modulated radiotherapy (IMRT). As margins become tighter around target volumes, the success of the treatment is increasingly dependent upon having the target volumes precisely situated in the intended locations. The use of high dose gradients to avoid radiation to sensitive structures means that slight shifts of these structures can subject them to large unintended doses.

The advent of on-line three-dimensional imaging for radiotherapy promises to vastly increase knowledge of patient anatomy at the time of treatment. It is important to have a knowledge of a patient's anatomy at the time of treatment. CT imaging is a particularly useful tool for verifying how a radiation dose was or is to be distributed with respect to the target volume and margin, and can detect if sensitive structures will be or are harmed by a shift in position. And since CT imaging is typically used for treatment planning, it is also an appropriate way to monitor the patient on a day-to-day basis. It would be particularly useful to have CT capability integrated into a radiotherapy system because this precludes the need to position a patient twice and thus, minimizes the likelihood of patient motion between imaging and treatment. It is also desirable to use image guidance for treatment verification before, during and after delivery to modify treatment plans. This process is referred to as image guided adaptive radiotherapy (IGART) and is an extension of adaptive radiotherapy (ART). In a broad sense, IGART seeks to incorporate feedback into the radiotherapy process to deliver the most appropriate treatment for a patient on any given day, and to remedy any imperfections in earlier fraction deliveries.

ART is a closed-loop radiation treatment process where the treatment plan can be modified using a systematic feedback of measurements. It improves radiation treatment by systematically monitoring treatment variations and incorporating them to reoptimize the treatment plan early on during the course of treatment. In the ART process, the field margin and treatment dose can be routinely customized to each individual patient to achieve a safe dose escalation.

Typical uses for on-line imaging includes rigid-body patient positioning, indication of changes in internal anatomy, calculation of delivered dose, either prospectively or retrospectively, and reoptimization of treatments, as necessary. Dose calculations and reoptimizations can be very time consuming, especially for complex IMRT treatment, making them virtually impossible to complete while the patient is on the treatment couch.

Accordingly, a need exists for a method for precisely delivering a dose of radiation to a tumor without the need for complete dose calculations or reoptimization.

SUMMARY OF THE INVENTION

The present invention provides methods to utilize on-line CT, or other fraction images, for improved treatment delivery without the need for complete dose calculations or reoptimization. On-line imaging enables daily imaging of the patient in the treatment position. Image-guided radiotherapy utilizes these images to direct or adapt treatments accordingly.

In one aspect of the present invention, a process herein referred to as contoured anatomy dose repositioning (CADR) is used to determine how to deliver proper radiation dose when it has been determined that anatomical changes from the plan are present. This is an automatic or semi-automatic way to determine how the patient should be shifted or the delivery should be modified to account for the anatomical changes based on the delineation of relevant anatomical structures. The CADR method provides an optimized position of the patient for which the desired targets and sensitive structures will be best situated in the dose distribution.

Once the relative locations are determined, the application of that shift can be made by either moving the patient, modifying the delivery to account for the shift, or using a combination of the two.

The necessary inputs to this process are: 1) the fraction CT image, 2) contours of relevant anatomical features in the fraction CT, 3) a dose distribution for the fraction CT, either calculated directly for the fraction CT, or calculated indirectly for the planning CT and aligned to match the fraction CT via registration, also referred to as image fusion.

The way in which the contours are obtained is not particular to this invention, and several methods are possible, including: 1) manual contouring, 2) automatic contouring, or 3) template-based contouring, as well as combinations of these methods.

Given these inputs, automatic fusion is used to find a new patient position for which the dose distribution better reaches the target regions and/or avoids sensitive structures. This is achieved by defining an object fusion that quantifies how successful a certain relative patient position is. The automatic fusion routine searches for a patient position that the object function regards as most successful. Thus, CADR uses an optimization process, in the form of automatic fusion, but this optimization is different in nature from the dose optimization process, and is also significantly faster, which is why it is more useful.

In another aspect of the invention, a process, herein referred to as multiple-margin optimization with daily selection (MMODS) is used to improve radiation delivery without reoptimization. During the initial optimization procedure, plans are optimized for several margins of various contours (e.g., tight, medium, loose, etc.), or with different objectives (e.g., aggressive treatment, sensitive structure sparing, etc.). Similarly, if multiple patient image sets are available, or as they become available, plans can be optimized for the different anatomical layouts, either using current information, or accumulated information regarding the superposition of organ locations in the combination of images. The physician can then choose in real time from a variety of optimized plans, generally with different margins, during the treatment process, and thereby compensate for a recognized change in size or position of the tumor or neighboring tissue.

When doing treatment delivery optimization on the planning images, contours are drawn to include different possible margins about the targets and sensitive structures. For example, contours with small margins about targets can most closely conform to the size and shape of those targets, but will be most sensitive to imprecision and organ motion. MMODS optimizes plans for several different margin sizes or contourings. Then, on any given day of the treatment, a user can decide which plans to deliver. Based on how the internal anatomy changes, it may be prudent to use a plan with a larger margin to better encompass the treatment regions, or a smaller margin may be desired because of the increased proximity of a target region and a sensitive structure on that day.

A primary benefit of MMODS is that it does not require reoptimization. Instead, several approved plans are available, and for each fraction an appropriate delivery plan is chosen. While MMODS can function independently of CADR, they are also well suited to work in tandem. For example, an improved patient positioning indicated by CADR may allow the selection of a plan with smaller margins than otherwise needed. Or if larger margins are desired, CADR may help accommodate that without additional harm to sensitive structures.

The MMODS embodiment provides multi-margin optimization with daily selection without the need for reoptimization or daily contouring. Instead of selecting a single planning target volume (PTV) margin that will provide adequate target coverage for all days of a treatment, plans are optimized and approved for multiple PTV margins. On-line CT imaging is used to inspect the daily anatomy of a patient and select the margin necessary to cover the target while minimizing dose to sensitive structures.

The goal of MMODS is to utilize on-line images to balance target coverage and sensitive structure avoidance based on daily anatomical information. Multiple plans are pre-optimized using different margins. On each treatment day, the on-line images are used to select the plan and margin necessary for target coverage. MMODS does not require daily contouring or reoptimization, and only marginally increases the time a patient is on the treatment table.

MMODS and CADR can be used independently, or together. CADR results will generally determine how best to reposition the patient with respect the gantry, although this repositioning can be achieved in practice by either moving the patient or adjusting the treatment delivery. If the CADR results do not reproduce the planned dose distribution as well as desired, other appropriate plans (MMODS) can be selected, potentially utilizing other margin selections, to better account for the patient's anatomy that day, derived by various techniques such as on-line CT. This process can be iterated, until the preferred combination of a patient position (CADR) and desired plan (MMODS) is identified.

In yet another aspect of the invention, an improved adaptive radiotherapy treatment method is contemplated.

Various embodiments of the present invention are achieved by using different registration techniques. Basically, the planning image and fraction image are aligned to determine what modification is needed before treatment. This registration is preferably performed by fusion, which may be automated or semi-automated.

By using the methods of the present invention, it is possible to: a) duplicate or more closely achieve planned radiation doses for different structures; b) mitigate degradation of sensitive tissue due to anatomy changes; and c) modify doses received through adaptive radiotherapy.

While the present invention is particularly useful for intensity modulated radiation therapy, other applications are possible and references to use with image guided adaptive radiotherapy using equipment having on-line CT capability should not be deemed to limit the application of the present invention. The present invention may be advantageously adapted for use where similar performance capabilities and characteristics are desired such as in adaptive radiotherapy or the like.

Various other features, objects, and advantages of the invention will be made apparent to those skilled in the art from the following detailed description, claims, and accompanying drawings.

BRIEF DESCRIPTION OF THE DRAWINGS

FIG. 3 is a schematic drawing of a patient having an internal structure and a dose target;

FIG. 4 is a schematic drawing of the patient showing the dose target in an altered position with respect to the patient;

FIG. 5 is a schematic drawing of the patient showing the result of a realignment of a respositioned dose target as a result of patient movement in accordance with an embodiment of the present invention;

FIG. 11 is a block diagram of an improved adaptive radiotherapy method in accordance with yet another embodiment of the present invention.

DETAILED DESCRIPTION OF THE INVENTION

Figure 1:
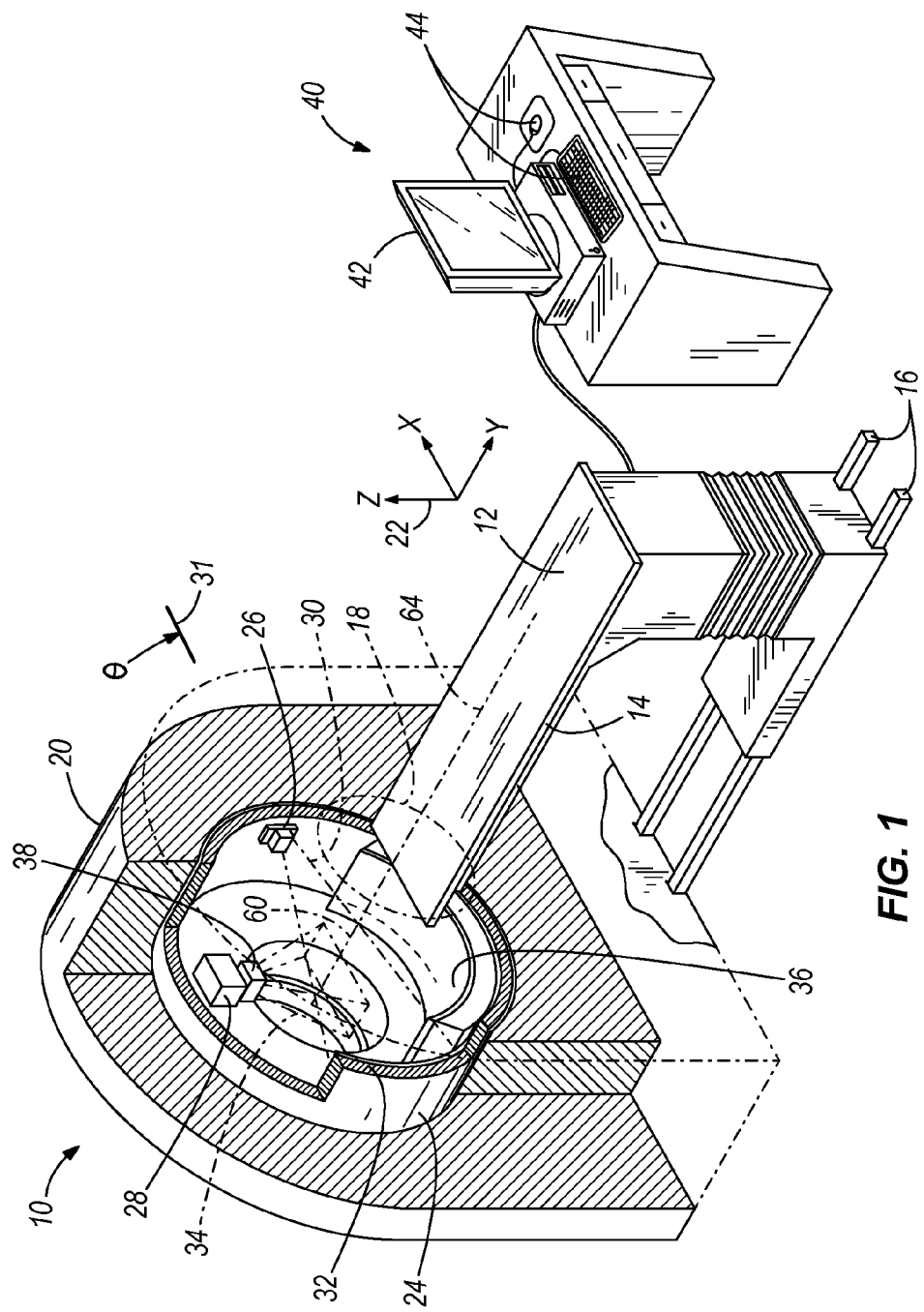
FIG. 1 is a perspective, cut-away view of a radiation therapy system providing for the acquisition of radiographic projections and for the generation of high energy radiation therapy.

Referring now to FIG. 1, a radiation therapy machine 10, suitable for use with the present invention, includes a radiotranslucent table 12 having a cantilevered top 14. The table top 14 is received within a bore 18 of an annular housing 20 of the radiation therapy machine 10 with movement of the table 12 along tracks 16 extending along a z-axis of a Cartesian coordinate system 22.

Table 12 also includes an internal track assembly and elevator (not shown) to allow adjustment of the top 14 in a lateral horizontal position (indicated by the x-axis of the coordinate system 22) and vertically (indicated by the y-axis of the coordinate system 22). Motion in the x and y directions are limited by the diameter of the bore 18.

A rotating gantry 24, coaxial with the bore 18 and positioned within the housing 20, supports an x-ray source 26 and a high energy radiation source 28 on its inner surface. The x-ray source 26 may be a conventional rotating anode x-ray tube, while the radiation source 28 may be any source of treatment radiation including one producing x-rays, accelerated electrons, protons or heavy ions such as are understood in the art. The x-ray source 26 and a radiation source 28 rotate with the gantry 24 about a center of rotation 64 near the top of patient table 12 when the table top 14 is positioned within the bore 18.

The x-ray source 26 is collimated to produce a fan beam 30 lying generally within the x-y plane and crossing the bore 18 and thus the table top 14 when table top 14 is positioned within the bore 18. The fan beam 30 diverges about a central axis 31 whose angle is controlled by the position of the gantry 24. The axis 31 will henceforth be termed the projection axis.

After exiting the table top 14, the fan beam 30 is received by a linear array detector 32 positioned diametrically across from the radiation source 28. Thus, the rotating gantry 24 permits fan beam radiographic projections of a patient on the table top 14 to be acquired at a variety of angles about the patient.

The radiation source 28 is mounted so as to project a fan beam of high energy radiation 34, similar to the fan beam 30, but crossing fan beam 30 at right angles so as to be received on the other side of the gantry 24 by radiation detector and stop 36. In an alternative embodiment, the stop is replaced by a detector to provide an alternative to the detector 32 for deducing motion of the patient. The fan beam of high energy radiation 34 diverges about a radiation axis centered within the beam and perpendicular to the projection axis 31.

The radiation source 28 has a collimator 38 mounted in front of it to divide the beam of high energy radiation 34 into multiple adjacent rays whose energy and/or fluence may be individually controlled.

A computer 40 having a display screen 42 and user entry mouse and keyboard 44 well known in the art is connected to the radiation therapy machine 10 to control motion of the table 12 and to coordinate operation of the gantry 24 together with the radiation source 28 and x-ray source 26 and to collect data from the linear array detector 32 during a scan of the patient according to methods well know in the art.

Figure 2:
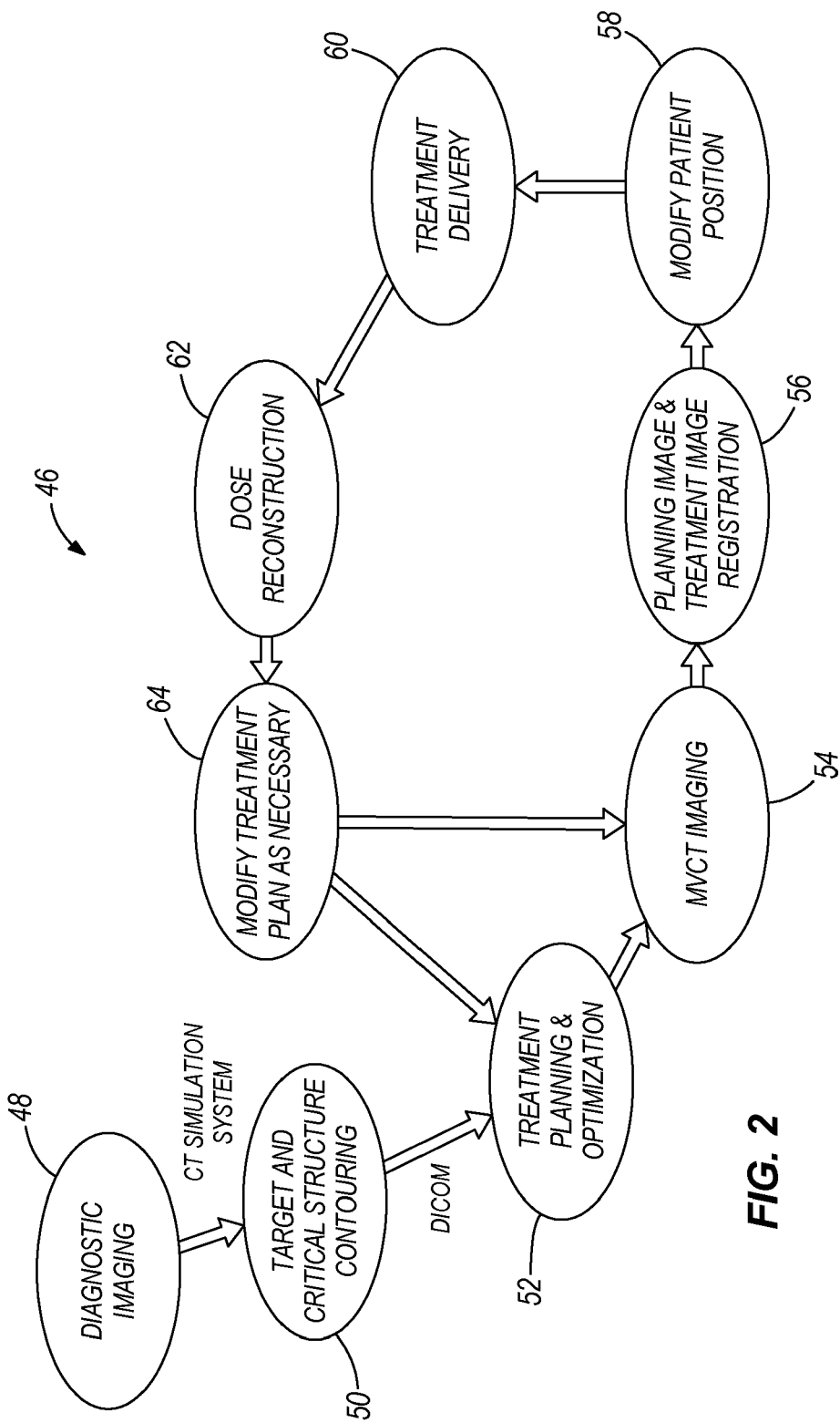
FIG. 2 is a block diagram of a radiation treatment method of the present invention.

FIG. 2 is a block diagram of a radiation treatment method of the present invention.

The method of the present invention uses on-line CT or other means of obtaining fraction images to improve the delivery of radiation to a target structure without complete reoptimization of a radiation therapy plan. More particularly, when a patient's pretreatment set-up position and internal anatomy positions for a prescribed fraction differ from the planning position by only rigid-body rotations and translations, then these patient offsets can be determined using existing methods, and likewise corrected either by moving the patient, or modifying the delivery to reflect the displaced position. However, in the case of internal anatomy changes, the "correct" patient repositioning dictated by conventional methods may not result in the desired dose distribution to any targets and sensitive structures. Instead, one may use CADR to move the patient to a preferable position (or translate the treatment) with regard to the dose distribution and/or use MMODS to select an alternate treatment plan that is more appropriate for achieving the desired dose distribution given the patient's current anatomy.

The necessary information needed to perform CADR is: 1) a fraction image, and 2) a dose distribution for the fraction image, either calculated directly therefrom, calculated indirectly and aligned to match the fraction image via registration or otherwise estimated. CADR may also require contours of relevant anatomical features in the fraction image, which may be obtained by any method, including, but not limited to manual contouring, automated contouring, deformable fusion, template-based automatic contouring, or a combination thereof. After the contours are determined, registration is performed between a combination of the planning image, planning contours, and planning dose distribution and a combination of the newly obtained fraction image, fraction contours, and fraction dose distribution. Registration is used to find a new patient position for which the dose distribution better reaches target volumes and/or avoids sensitive structures. This registration may be performed by a technique called fusion, and can utilize dose and contour information in addition to the image information commonly used to align images. The fusion process may be automated by defining a mathematical function that quantifies the success of a certain relative patient position. Preferably, an automatic fusion or deformable fusion routine is used to search for a patient position that the mathematical function regards as most successful.

In another embodiment of the present invention, a semi-automatic fusion method may be used to enable the physician to incorporate dosing preferences. For example, several functions may be created according to preferences (e.g., very aggressive treatment, greatest sparing of sensitive structures, etc.), and optimal patient repositioning could be determined for each function. The physician could then choose from those results. For further interaction, the physician could change the function, or any weighting applied to the different terms of the function.

In yet another embodiment, the fusion method could be further advanced by training the system with regard to preferred weights. In this embodiment of the present invention, the physician is presented with a series of choices between two possible dose distributions (based on relative patient displacements). Based on the physician's selections, the preferences regarding the weights in the objective function could be further defined. A single person could "train" multiple functions for different treatment sites or different treatment goals.

If a patient's set-up for a treatment fraction differs from the planning position by only rigid-body rotations and translations, then there are two basic methods to remedy the situation. One is to move the patient to the correct position. The other is to modify delivery parameters to account for the patient's current position. A hybrid approach is also possible. Theoretically, either technique could perfectly restore the planned delivery, although in practice there are some limits from the imprecisions the repositioning and delivery modification.

However, if a patient's anatomy has changed, then methods for repositioniong and/or delivery modification are less obvious, shy of contouring and reoptimization as mentioned above. Nonetheless, one can use the planned delivery and the fraction CT to calculate the dose that would be delivered for the patient's current position. Similarly, one could estimate the dose that would be delivered to the patient in the current position by modifying the planned dose delivery. Image registration between the planning and fraction images could determine their relative alignment. Then applying the same transformation to the originally planned three-dimensional dose distribution would show how it was received by the structures in the fraction image. There is a generally small imprecision in using this latter approach because the dose calculation will not be based on the most current patient representation. Nonetheless, the larger concern is not so much how the dose calculation changes in terms of dose deposited to each location in space, but the locations of targets and sensitive structures relative to the dose deposition.

The same concept applies to small shifts in the patient's position. The dose distribution in physical space is not significantly affected, but the structures in the patient that receive those doses may change a lot. A simple example is shown in FIGS. 3-5. A treatment delivery is planned to deliver a high dose of radiation to an internal region inside the patient, as shown in FIG. 3. However, as shown in FIG. 4, the structure has moved relative to the rest of the patient, moving it away from where the dose is delivered. The anatomy shifts, as revealed in a fraction image, such that the treatment region is displaced relative to the rest of the patient. If the patient is set-up "correctly" based on the patient's boundary, then the dose distribution in physical space will be virtually unchanged, dotted ring in FIG. 4, from where it was intended. Yet this distribution will no longer reflect the location of the intended treatment region. However, by shifting the entire patient, as shown in FIG. 5, to the left, the target region will again be in the region of high dose, with the patient's original position indicated by the dashed line. The change to the dose calculation from such a shift will be generally small, whereas the effect on whether targets get hit, or sensitive structures are avoided, is much greater.

Referring again to FIGS. 3 and 4, it is demonstrated how the dose distribution to the target volume can be significantly affected by physical changes in the patient. In FIG. 3, a treatment delivery is planned to deliver a high dose to a dose target 68 in a patient body 66. In the fraction image of FIG. 4, the internal region 66 has shifted relative to the rest of the patient body 66. During treatment set-up, if the patient body 66 were aligned in accordance with the treatment plan, the dose distribution will no longer reflect the location of the intended treatment region.

If the entire patient body 66 is shifted appropriately the dose target 68 may be aligned to receive a preferable dose. (See FIG. 5 with the patient's original position indicated by the dashed line). The CADR process seeks a patient position that achieves this preferable dose, and can utilize not only image information, but also dose and contour information to determine this position. Consider that this body shift may bring sensitive structures into play that were not previously considered, and so any such structures are also included in the optimized repositioning. The dose information needed for the fraction image can be calculated directly, estimated, or indirectly computed by transforming the planned three-dimensional dose distribution based upon the relative image alignments. Though a small imprecision in dose calculation (in terms of dose deposited to each location in space), can occur because the dose calculation will not be based on the most current patient representation, such imprecision is insignificant as compared to the potential under-or over-dosing of the target and surrounding structures. Rather than shift the entire patient body, if the radiation delivery system allows, the entire treatment may instead be translated to more conveniently achieve an equivalent result.

The entire CADR process may be automated, including the fusion process. Some typical mathematical functions used for fusion or registration include terms for integral doses, first and second moments of the differential dose volume histograms (DDVHs), absolute differences and exponentiated differences between planned and potential DVHs, and percent-volume of a structure receiving above or below certain doses. These different metrics are often weighted and combined with terms for each contoured structure. The combination of these or other terms can provide a single function that can be optimized for automatic CADR.

Adjustments may also be made using multiple-margin optimization with daily selection (MMODS). In MMODS, contours are drawn during the optimization process to generate different possible margins about the target structures and sensitive structures. For example, contours with small margins about targets can most closely conform to the size and shape of those targets, but will be most sensitive to imprecision and organ motion. MMODS is used to optimize plans for several different margin sizes or contours. Thus, on any given day of the treatment, the physician can decide which optimized plan to deliver. Depending on how the patients internal anatomy changes, it may be prudent to use a plan with a larger margin to better encompass the treatment structures; or it may be prudent to use a plan with a smaller margin because a target structure may be in closer proximity to a sensitive structure on the day of treatment. A primary benefit of MMODS is that it does not require complete re-optimization at the time of treatment. Instead, several optimized plans are available, and for each fraction, an appropriate delivery plan is chosen.

Figure 6:
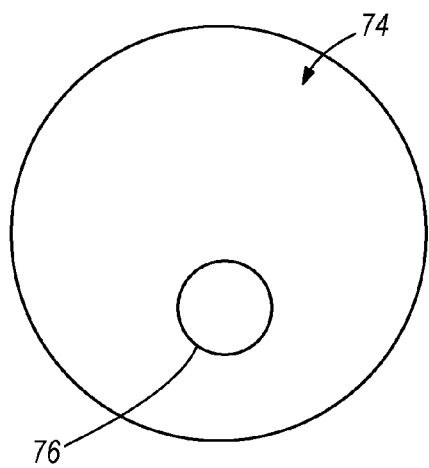
FIG. 6 is a schematic drawing of a patient having an internal structure and a dose target similar to FIG. 3.
Figure 7:
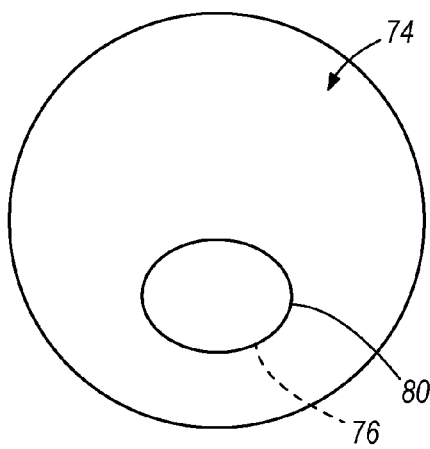
FIG. 7 is a schematic drawing of the patient showing an enlarged dose target.
Figure 8:
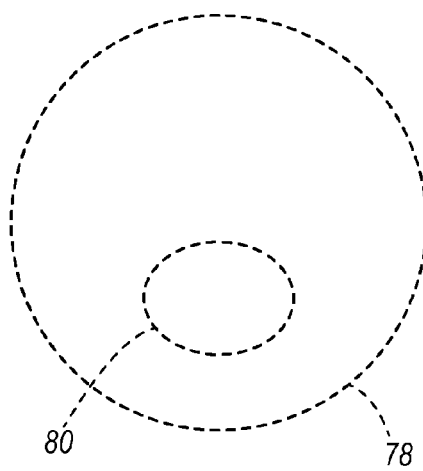
FIG. 8 is a schematic drawing of a dose target margin.
Figure 9:
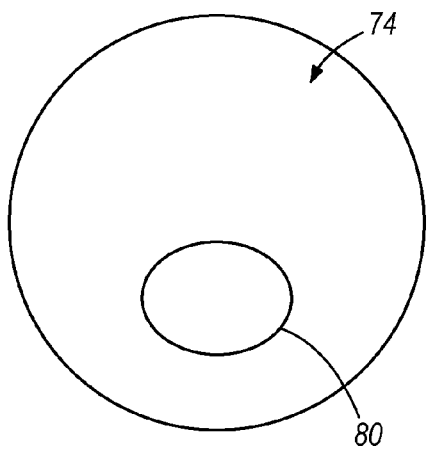
FIG. 9 is a schematic drawing of the patient showing the dose target margin superimposed on the internal structure and dose target of FIG. 7 to properly cover the dose target of the patient in accordance with another embodiment of the present invention.

FIG. 6 is a schematic drawing of a patient having an internal structure and a dose target similar to FIG. 3. FIG. 7 is a schematic drawing of the patient showing an enlarged dose target. FIG. 8 is a schematic drawing of a dose target margin. FIG. 9 is a schematic drawing of the patient showing the dose target margin superimposed on the internal structure and dose target of FIG. 7 to properly cover the dose target of the patient in accordance with another embodiment of the present invention.

A similar implementation of MMODS would be to optimize one or more treatments during the planning stage, but also to optimize additional plans based upon images acquired using an on-line imaging system or other modality for obtaining more current anatomical or physiological representations of the patient. For example, additional optimizations might be based upon either the newest data sets, or upon accumulated information over multiple data sets. On each subsequent day, a treatment plan can be selected based upon whichever of the different planning images best resembles that day's fraction image, or based upon the set of contours that best cover the targets while avoiding sensitive structures. In this regard, any image or set of images that is used to generate a new treatment plan is considered a planning image. As an example of MMODS, the preferred contour for a given target region (including margin) might be the one shown in FIG. 6. However, knowing that target regions may change from day to day, an additional optimization is created for the larger target region shown in FIG. 7. Thus, if the fraction image FIG. 6 indicates that the target region has changed, MMODS plan with the expanded margin can be selected FIG. 8 to properly cover that day's target region.

The multi-margin optimization can be generated in such a way that the optimization with the smallest or a particular margin is minimally perturbed by including the optimization corresponding to the subsequent margin. This concept of a set of linked but independent optimizations allows the use of this technique during very short periods of time. For instance in cases where the anatomy can move during very short periods of time and the information about this movement is feedback to the delivery system, the pre-calculated optimization can be used to quickly adjust the margins of the treatment delivery. This additional optimization for extra complete or partial regions ultimately enables the treatment delivery to be rapidly modified to account for anatomy changes before or during delivery.

While MMODS and CADR can function independently of one another, the methods can be used together. For example, the improved patient positioning indicated by CADR may allow the selection of a plan with smaller margins than otherwise needed; or if larger margins are desired, CADR may help accommodate that without additional harm to sensitive structures.

A typical radiation treatment session using CADR and/or MMODS is performed in the following steps. (1) Obtain a new patient image to determine the relative location of the target and sensitive structures. (2) Compare prior treatment plan and MMODS plans to the new images and select an appropriate plan. (3) Adjust the patient position using CADR to better position the internal anatomy relative to the delivered dose. (4) Iterate as necessary, to best combine a treatment plan and a patient position to achieve the desired dose distribution. (5) Deliver the selected plan to the patient. This plan may include additional modifications to account for the rigid-body displacement dictated by CADR without need for physically moving the patient.

CADR, and the concept of optimized dose-based repositioning can use any appropriate object function. The object function can be adjusted to different tasks or preferences, with weights for target coverage, sensitive structure dose, etc. Common CADR objective function terms include least-squares differences, moments, minimum/maximum DVH points.

This invention is not specific to a single objective function, but regards the use of automatic fusion with an object function to determine an improved patient position relative to the planned dose delivery, which could be implemented either by changing the patient position or by modifying the treatment delivery to account for the desired shifts or rotations.

Some typical object functions that have been used include terms for integral doses, first and second moments of the differential dose volume histograms (DDVHs), absolute differences and exponentiated differences between planned and potential dose volume histograms (DVHs), and percent-volume of a structure receiving above or below certain doses. These different metrics are often weighted and combined, with terms for each contoured structure.

The combination of these or other terms can provide a single objective function that can be optimized for automatic CADR. However, a semi-automatic approach may also be used to enable the user to incorporate preferences. For example, several objective functions may be created (e.g., very aggressive treatment, greatest of sparring of sensitive structures, etc.) and an optimal patient repositioning could be determined for each. The user could then choose from those results.

For further interaction, the user could change the objective function, or the weights applied to the different terms of that function. For example, the user might indicate different relative importances of the doses hitting different structures.

This concept could be further advanced by training the system with regard to a user's preferred weights. The user could be presented with a series of choices between two possible dose distributions based on relative patient displacements. Based on the user's selections, the user's preferences regarding the weights in the object functions could be honed. A single user could also train multiple objective functions for different treatment sites or different treatment goals.

This daily position optimization process takes seconds, as opposed to full re-optimization, which can take substantially longer. CADR is preferable to external fiducial or bony-anatomy repositioning, because it accounts for displacements of targets and sensitive structures relative to bones or fiducials. Results indicate that CADR can improve upon the DVH's that would be expected with fiducial or bony-anatomy based positioning amidst internal anatomy changes.

Figure 10:
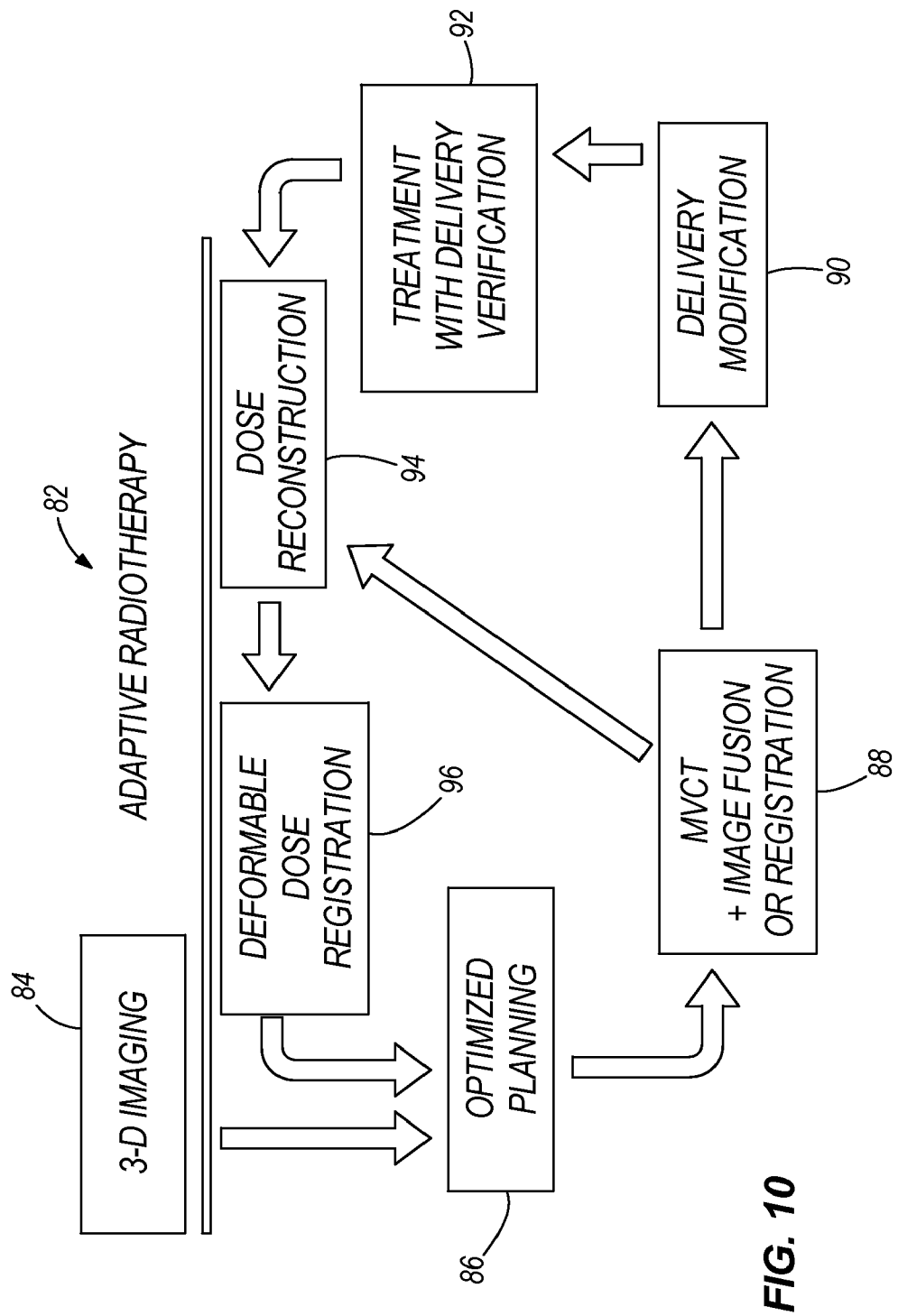
FIG. 10 is a block diagram of an adaptive radiotherapy method.

FIG. 10 is a block diagram of an adaptive radiotherapy method.

FIG. 11 is a block diagram of an improved adaptive radiotherapy method in accordance with yet another embodiment of the present invention.

There have been many proposals to address the Adaptive Radiation Therapy (ART) process. This is the process of adapting each treatment fraction while maintaining a physician's prescription. An embodiment of the present invention provides an optimized process for ART. It is a knowledge-based system that leverages unique tomotherapy features.

As shown in the FIG. 11, the process of using high quality diagnostic images (Box 1, $CT_{Diag}$), contouring (Box 2), and plan/optimization (Box 3) are well known processes in the delivery of modern IMRT treatments. The process of acquiring verification CT images Box 4, $VRCT_{Frac(d1)}$) for first day fraction (d1, and subsequent days (dn)), for the purpose of verifying the treatment position, is a process unique to the present invention. The use of on-line CT imaging capability gives the user the option of electronically fusing (Box 5) the $CT_{Diag}$ image with the $VRCT_{Frac(d1)}$ image to determine patient set-up errors (Box 7). The VRCT image also provides important information related to critical structure motion. This embodiment uses these daily VRCT images to track target and critical structure motion. Each fraction requiring a VRCT increases the system knowledge-base, thereby increasing ART options.

Referring back to FIG. 11, on the first day of treatment, the system would load the $CT_{Diag}$ plan and treat (Box 9 and 10). No ART is possible because there are no VRCTs in the database. After the treatment, and at some off-line time, a new plan could be developed using the verification image $VRCT_{Frac(d1)}$ (Box 13 and 14). The plan would be based on the original physician prescription for treatment and stored (Box 16). At this point, multi-contour margins may be developed by interpolating from $CT_{Diag}$ to $VRCT_{Frac(d1)}$. This process could also include a physician review option (Box 15).

On the second day, the system would begin the process of comparing, via fusion methods, $VRCT_{Frac(d2)}$ image with $VRCT_{Frac(d1)}$ and $CT_{Diag}$ to determine best fit characteristics (Box 11). The best fit would determine the best plan to be used. The system would continue to learn with each VRCT and as time progressed, the system would accumulate many optimized plans, based on the physician's original prescription (including DVH constraints), providing the best ART treatment.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

We claim:

1. A method for achieving a desired dose distribution comprising:
   obtaining at least one treatment planning image from a patient to determine the relative location of target and sensitive structures;
   preparing a treatment plan for the patient based on the at least one treatment planning image, the treatment plan including a planned dose distribution;
   obtaining at least one three-dimensional image from the patient in substantially a treatment position, the three-dimensional image including anatomical data and being used for volumetric dose calculations;
   comparing the at least one treatment planning image and the at least one three-dimensional image; and
   adjusting how the dose is received by the patient based on the comparison.

2. The method of claim 1 wherein the planned dose distribution for the patient is based on the treatment plan.

3. The method of claim 2, wherein the planned dose distribution is based on the at least one three-dimensional image of the patient in substantially a treatment position.

4. The method of claim 1 further comprising repositioning the planned dose distribution for the patient based on the at least one three-dimensional image of the patient in substantially a treatment position.

5. The method of claim 1 further comprising modifying the treatment plan and the planned dose distribution.

6. The method of claim 1 further comprising adjusting patient position to better position patient's internal anatomy relative to the planned dose distribution.

7. The method of claim 1, wherein the planned dose distribution is modified to take into account changes in patient position and/or changes in patient anatomy.

8. The method of claim 1, further comprising selecting a treatment plan from a plurality of preexisting plans for the patient based on the three-dimensional image acquired from the patient at the time of treatment delivery.

9. The method of claim 8, wherein multiple plans created with objective functions are used for treatment delivery.

10. The method of claim 1, wherein objective functions and weightings are adjusted to fine-tune treatment delivery.

11. The method of claim 1, wherein objective function weights are learned.

12. The method of claim 1, wherein the output of the dose calculation is utilized to move the patient, modify treatment delivery, or some combination of the two.

13. The method of claim 12, wherein the treatment plan includes initially available images and related treatment plans and images obtained subsequent to initial planning.

14. The method of claim 1, further comprising generating contours on one of the target and sensitive structures by one of manual contouring, automated contouring, deformable fusion, template-based automatic contouring, and a combination thereof.

15. The method of claim 1, wherein adjusting how the dose is received by the patient includes repositioning the patient to improve the dose distribution.

16. The method of claim 1, wherein the images of the patient are obtained using one of non-quantitative CT, MRI, PET, SPECT, ultrasound, transmission imaging, fluoroscopy, and RF-based localization.

17. The method of claim 1, wherein adjusting how the dose is received by the patient includes utilizing one of image information, contour information, dose-volume histograms, and dosimetric information to reposition the patient.

18. A method of delivering radiation therapy, the method comprising:
   acquiring a first image of a region of interest in a patient;
   generating a plurality of radiation treatment plans for the patient based on the first image;
   acquiring a second image of the region of interest while the patient is in substantially a treatment position, the second image being at least three-dimensional and including anatomical data; and selecting one of the radiation treatment plans based at least in part on dosimetric information from the second image.

19. The method of claim 18 further comprising generating a different radiation treatment plan based on a different position of the region of interest than the position of the region of interest in the first image and the second image.

20. The method of claim 18 further comprising comparing a position of the region of interest in the first image to a position of the region of interest in the second image.

21. The method of claim 18 wherein each of the radiation treatment plans includes a contour defining a margin around the region of interest based on the position of the region of interest in the first image.

22. The method of claim 18 wherein the second image is adequate for dose calculations.

23. A method of delivering radiation therapy, the method comprising:
   acquiring a first image of a patient;
   generating a radiation treatment plan for the patient, the radiation treatment plan based on the first image;
   acquiring a second image of the patient substantially in a treatment position, the second image being three-dimensional and suitable for three-dimensional contouring;
   generating a contour on the second image; and
   identifying a patient position with respect to a radiation delivery device based on dosimetric information and the contour.

24. The method of claim 23 wherein the second image is suitable for dose calculations.

25. The method of claim 24 wherein identifying a patient position is further based on the dose calculations.

26. The method of claim 23 further comprising generating a plurality of treatment plans based at least in part on the first image.

27. The method of claim 26 further comprising selecting one of the treatment plans for delivery to the patient, the selected treatment plan based on a desired patient position.

28. The method of claim 23 wherein the dosimetric information is determined from the first image.

29. The method of claim 23 wherein the dosimetric information is determined from the second image.

30. The method of claim 23 wherein the dosimetric information is determined from a combination of the first image and the second image.

* * * * *

UNITED STATES PATENT AND TRADEMARK OFFICE
CERTIFICATE OF CORRECTION

PATENT NO.       : 8,406,844 B2
APPLICATION NO.  : 10/506866
DATED            : March 26, 2013
INVENTOR(S)      : Ruchala et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1886 days.

Signed and Sealed this
First Day of September, 2015

Michelle K. Lee
*Director of the United States Patent and Trademark Office*